United States Patent [19]

Marx

[11] 3,996,928
[45] Dec. 14, 1976

[54] PATIENT VITAL-SIGNS AUTOMATED MEASURING APPARATUS

[76] Inventor: Alvin J. Marx, 315 College Road, Bronx, N.Y. 10471

[22] Filed: May 28, 1975

[21] Appl. No.: 581,489

[52] U.S. Cl. .................. 128/2.05 A; 128/2.05 Q; 128/2.08; 128/DIG. 29
[51] Int. Cl.² ...................................... A61B 5/02
[58] Field of Search ............. 128/2 H, 5 C, 2.05 A, 128/2.05 M, 2.05 P, 2.05 Q, 2.05 R, 2.05 T, 2.06 A, 2.06 F, 2.06 R, 2.08, 2.1 R, DIG. 29

[56] References Cited
UNITED STATES PATENTS

| | | | |
|---|---|---|---|
| 3,374,461 | 3/1968 | Anderholm | 128/2.05 Q |
| 3,414,896 | 12/1968 | Glick et al. | 128/2.08 |
| 3,857,385 | 12/1974 | Hampl | 128/2.08 |

*Primary Examiner*—William E. Kamm
*Attorney, Agent, or Firm*—Stephen B. Judlowe

[57] ABSTRACT

Automated electronic medical vital-sign measuring and recording system apparatus includes plural transducers and signal processing channels for sequentially multiplexing the monitored patient characterizing physical parameter values onto an output record — e.g., a printed tape. The system includes manual entry facilities to enter patient identification information and the like into the printed output record, and circuitry is included to treat interdependencies regarding the monitored physical characteristics.

14 Claims, 4 Drawing Figures

PATIENT VITAL-SIGNS AUTOMATED MEASURING APPARATUS

This invention relates to medical electronics and, more specifically, to improved integrated diagnostic equipment for automatically providing a display (e.g., print-out) of a patient's major vital signs.

It is an object of the present invention to provide improved medical diagnostic-vital signs monitoring apparatus.

More specifically, it is an object of the present invention to provide improved vital signs testing apparatus which is integrated, portable and readily utilized; which is automatically operative; which effects measurements in an improved manner; which multiplexes its several measurements onto an output record, and generally, which greatly facilitates and speeds up patient vital signs work up by heavily taxed medical personnel.

The above and other objects of the present invention are realized in specific, illustrative automated vital signs measuring and recording apparatus which produces an output record, e.g., a tape or sheet print out, of the so-called "vital signs" of a monitored patient, e.g., respiration rate, blood pressure, temperature, pulse rate and the like.

A keyboard is employed to enter alpha-numeric information such as patient identity, and plural transducer and transducer-produced signal processing channels to monitor the patient-characterizing parameters. Under control of a time base sequencer, the transducer channels are periodically and sequentially interrogated, and the reported parameter values multiplexed through to a printer or the like for output display and/or recording.

The above and other features and advantages of the present invention will become more clear from the following detailed description of a specific illustrative vital signs diagnostic measuring and recording apparatus, described in detail hereinbelow in conjunction with the accompanying drawing, in which.

Figure 1:
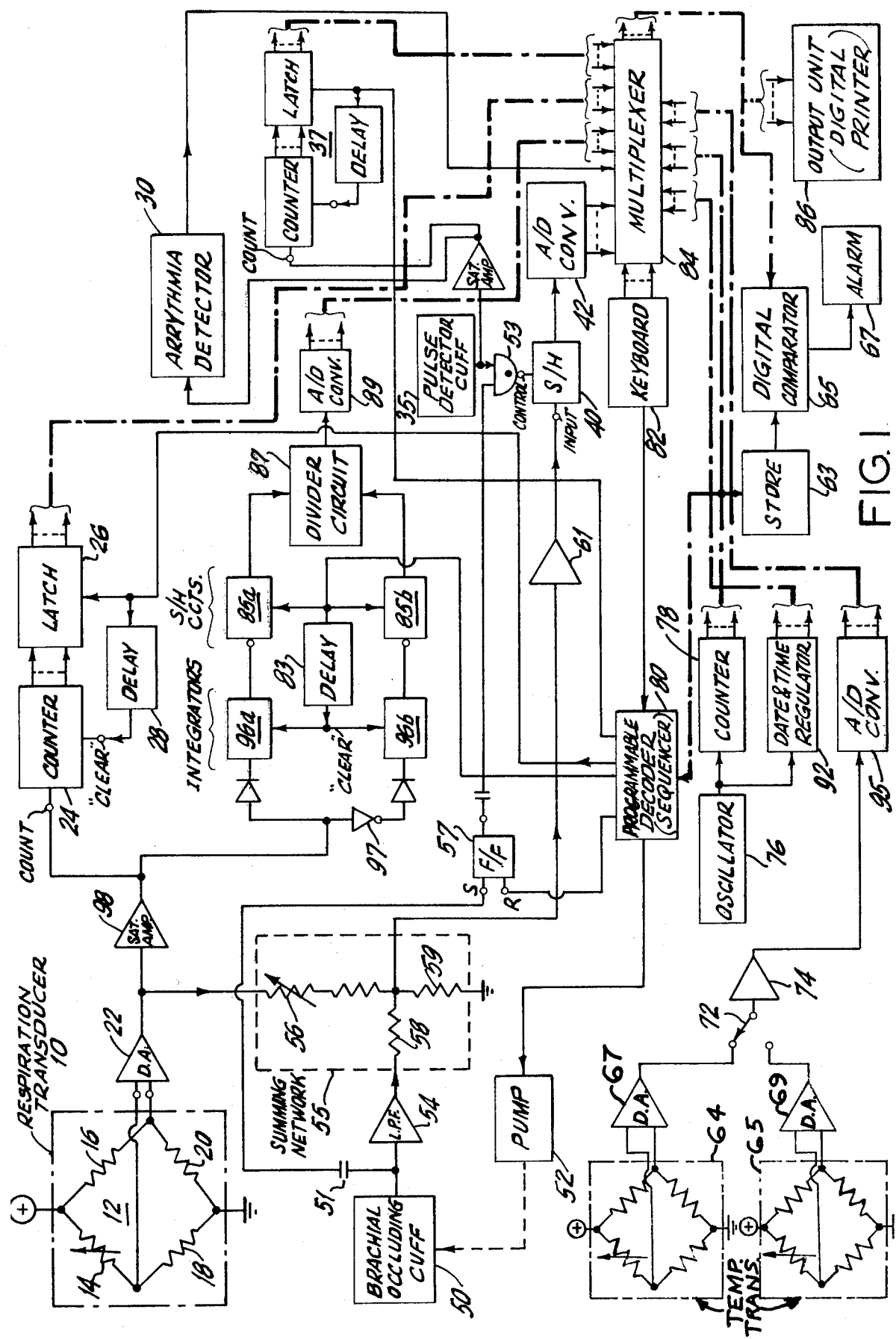
FIG. 1 is a block diagram schematically illustrating the basic electronic functioning of patient-monitoring vital signs measuring equipment embodying the principles of the present invention.
Figure 3:
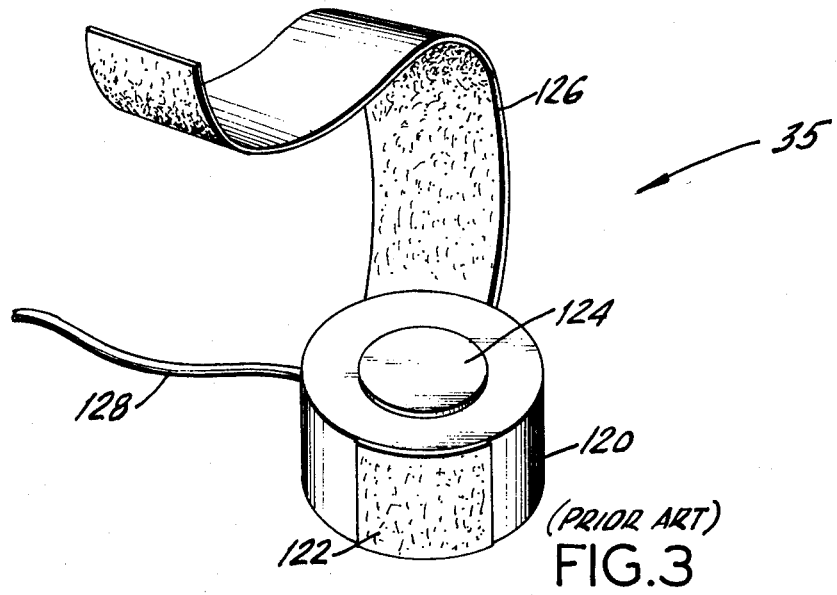
Figure 4:
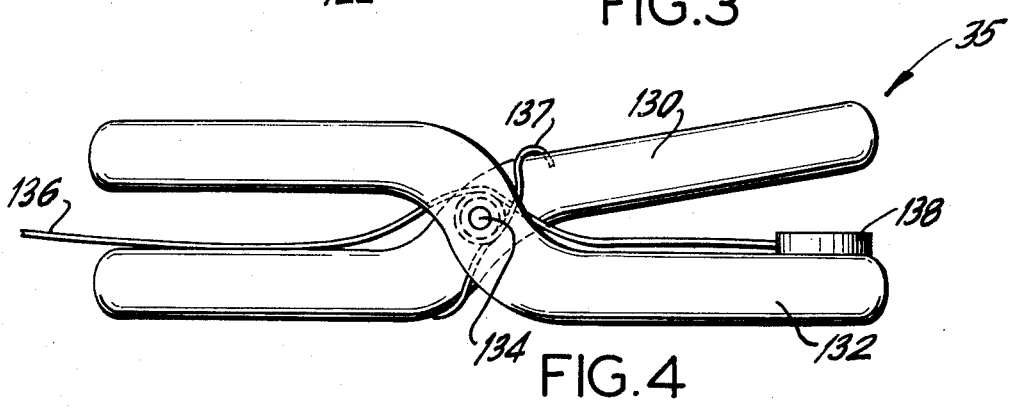

FIG. 3 depicts a prior art detecting cuff 35 employed to sample measurements from the cuff 50 during the peak pressure interval to obviate spurious blood pressure measurements; and FIG. 4 is an alternative embodiment for the detecting cuff 35 of the FIG. 1 arrangement.

Referring now to the drawing, and in particular, FIG. 1, there is shown an electronic system for automatically measuring and reporting the vital signs of a patient being monitored. By way of overview, several transducers discussed below (or an appropriate subset thereof) are attached to a patient; and may be left in place for an extended period of time where continuous patient monitoring is required. In accordance with one aspect of the invention, the apparatus may also automatically provide an output alarm indication when any monitored patient parameter falls outside a permissible bound therefor.

The several transducers each provide a binary quantification of an associated vital sign of a patient. These digital values are supplied as inputs to a multiplexer 84, as is alpha-numeric information (e.g., patient identity) generated at an operator console keyboard 82 and time and date information provided by a counter or counter-register 92. The multiplexer 84 is controlled by the output of a counter 78 which, in turn, is cycled by a master time base oscillator 76. Under control of the parameter specifying output of the counter 78, one of the multiplexer 84 digital input words is coupled to the output of the multiplexer 84 and supplied therefrom via a bus to the input of an output unit 86, e.g., a digital printer. Thus, as the counter 78 advances through its several states by reason of pulses supplied therefrom by the oscillator 76, information regarding the several patient parameters is sequentially fed for recording onto an output tape, paper record or the like at printer 86, together with the alpha-numeric header information supplied by the keyboard 82 and the contents of the date and time register 92. The element 92 may most simply comprise the well known digital clock cascade counter construction which may also be advanced by the oscillator 76.

Examining now the several transducer channels, there is included a respiration transducer 10 which includes a bridge 12 for supplying a signal indicative of a patient's respiratory phase. As employed in the instant invention, the respiration-indicative information comprises the subject's breathing rate, and also the relative dwell periods of the breathing operation into inspiration and expiration periods.

The bridge 12 includes fixed resistors 16, 18 and 20, and a variable resistance 14, e.g., a heated wire placed in proximity to a patient's nostrill which is periodically cooled by a subject's exhaling air flow. The variable resistor 14 may be physically affixed to a variable resistance element which serves as an oral temperature transducer 65 which is placed in a patient's mouth, the respiration element 14 being disposed to then be in proximity to the subject's nostrils. Where extended respiration monitoring is desired a separate respiration transducer is desirable.

Again focusing on, the respiration transducer 10, the air flow during exhalation cools the heated anemometer wire 14, thereby unbalancing the bridge 12, thus also unbalancing the inputs to a difference amplifier 22 which provides an output signal dependent in amplitude upon the expiration air flow. The output wave form from the difference amplifier 20 effects three functions, viz., measures the respiration rate; serves as a correction factor for blood pressure measurements in a summing network 55; and determines the inspiration-/expiration ratio.

Again focusing on the basic respiration measurement, the voltage cycle outputs from the difference amplifier 92 (one voltage cycle for one complete respiration cycle) are quantized i.e., converted to binary form, in a saturable amplifier 98 and are supplied therefrom to a counter 24. The outputs from the several counter 24 stages are supplied as inputs to a latch (register) 26.

The basic system time base counter 78 supplies its output to a programmable state decoder 80 which repetitively generates a timed interval over which respiration counts are to be determined, e.g., 30 seconds. Alternatively, special cycle or rate instructions may be loaded into the decoder 80 by an operator at the keyboard 82. Each time the end of a measuring interval is signaled by the programmable decoder (sequencer) 80, the decoder 80 pulses the latch 26 which thus becomes loaded with the instantaneous count state for the counter 24. After a very short delay effected by a delay element 28 to avoid a race condition, the decoder 80 supplied pulse clears the counter 24 to begin the next respiration counting operation. Thus, the latch 26 stores the results of the last respiration cycle counting operation, while a new measurement is being taken (up dated) in the counter 24. The contents of the latch 26, i.e., the last available respiration measurement is supplied via a plural lead bus as one input to the multiplexer 84 for periodic outputing by the printer 86 in the manner above discussed.

The binary quantized output of the saturated amplifier 98 is also supplied to circuitry for determining the ratio of the inspiration/expiration periods — again another useful vital sign. This ratio is of use in characterizing such possible conditions as emphysema and other obstructive pulmonary diseases.

To this end, the output of the saturating amplifier (assumed positive during expiration) is integrated in an integrator 96a. Similarly, the inspiration interval signal (assumed low state output of the saturated amplifier 98) is inverted by an inverter 97 and integrated in an integrator 96b. At a time signalled periodically at the end of each measuring interval by a delayed decoder-sequencer 80 pulse, sample and hold analog circuits 85a and 85b are loaded with the instantaneously accumulated values from the integrators 96a and 96b, respectively. The integrators 96a and 96b are then cleared by delay element 93 to begin new measuring cycles of operation. Thus, the analog values stored in the sample and hold circuits 85a and 85b provide a measure of the accumulated times during which the subject was performing inspiration or expiration during the previous measurement cycles, respectively.

The outputs of the sample and hold circuits 85a and 85b are supplied as inputs to an analog divider circuit 87 which effects the requisite inspiration/expiration ratio. The analog ratio signal is converted to digital form by an analog-to-digital converter 89, the output of which supplies a digital representation of the desired ratio as one input to the multiplexer 84.

Turning now to blood pressure measurements, a cuff 50 for occluding the brachial artery is mounted on the subject's upper arm. The cuff 50 (considered hereinbelow in conjunction with FIG. 2 from a mechanical standpoint) includes a pneumatic portion for selectively occluding the brachial artery so that blood does not flow through the artery at any point during the heart pumping cycle-including contraction of the left heart ventricle when arterial pressure is at its maximum. The cuff 50 also includes a transducer for providing an electrical measure of the instantaneous cuff pressure. Such occluding cuffs, together with apparatus for automatically inflating and deflating same, are well known in the art per se, although improvements (only) over such art with respect to cuffs in accordance with the instant invention are described herein. See, for example, M. Croslin U.S. Pat. No. 3,581,734 issued June 1, 1971 or S. Gilford U.S. Pat. No. 2,827,040 issued Mar. 18, 1958, the disclosures of which are incorporated herein by reference.

To initiate a blood pressure reading cycle of operation, the sequencer 80 signals a pump 82 as by energizing a relay, closing a valve or the like. The pump causes an increase in pressure in the cuff 50, as by passing air from a pump expansion chamber (for smoothing) into the cuff to a pressure above that required to completely close the brachial artery during the entire heart cycle. It is further observed by way of preliminary discussion that the composite apparatus includes detecting cuff 35 (e.g., a finger cuff used on the arm opposite to that on which blood pressure is being taken) for signalling the maximum blood pressure point independent of the cuff 50, as well as a capacitor 51 which passes only the A.C. voltage signals detected by the electrical transducer in the cuff 50, e.g., a piezoelectric element. These AC perturbations superimposed on the cuff occluding pressure signal comprise the well known Korotkoff signals which appear in an artery which is occluded during part of the heart cycle, but where the peak heart pressure exceeds the externally-applied occluding pressure to therefore permit pulsed blood flow.

With the above preliminary discussion in mind, a review of the blood pressure cycle of operation will now be considered. The pump 52 initially supplies an air over-pressure in the cuff 50 such that the artery is fully occluded. Thus, no blood flows in the occluded artery during any part of the heart cycle. Air slowly leaks from the occluding cuff 50 in any manner known in the art and disclosed by prior automated blood pressure apparatus, e.g., by employing a valve to permit air to escape at a fixed, relatively slow rate.

Eventually there comes a point where the maximum heart pressure during left ventricular contraction exceeds the instantaneous occluding pressure, and blood flows during a narrow time interval. The blood flow through the previously occluded artery results in the incidence of the so-called Korotkoff sounds (with an attendant pressure wave) which are detected by the transducer (the assumed piezoelectric element). This AC perturbation passes through the DC blocking capacitor 51 and partially enables an AND gate 53 via the differentiated output of a set flip-flop 57. The gate 53 is fully enabled during the proper peak pulse interval by the distal detecting cuff 35. The switched gate 53 signals a sample and hold circuit 40 which accepts the instantaneous analog signal then present at the input terminal thereof. This input signal, in turn, comprises the then prevailing occluding pressure signalled by the cuff 50 via low pass filter-amplifier 54, the summing network 55, and an amplifier 61. Thus, the sample and hold circuit 40 is loaded with an analog measure of the patient's systolic blood pressure i.e., the pressure when blood first appears in the artery. This value is preserved, notwithstanding future blood flow cycles by the flip-flop 57 which provides an AND gate 53 enabling signal only for the first incidence of the blood pulse (Korotkoff sounds).

In accordance with one aspect of the present invention, the analog occluding pressure value reporting by the cuff 50 is linearly combined (in summing network 55) with a correcting analog signal from the respiration measuring circuitry, blood pressure requiring a positive correction if a patient is in an inspiratory phase (positive intrathoracic pressure) vis-a-vis expiration. The correction signal flows via a resistor 56 to the summing node of the network 55 across a resistor 59, thereby adding a corrective value to account for the state of the thoracic cavity, to the basic, "raw" systolic pressure value signalled via a resistor 58.

As before, the patient's systolic pressure stored in analog form in the sample and hold network 40 is converted to digital form by an analog-to-digital converter 42, and is supplied therefrom as an input to the multiplexer 84. In a manner similar to the foregoing, and as set forth in said Croslin and Gilford patents, a subject's diastolic pressure may be similarly determined.

To measure heart rate, a counter-latch-delay circuit network 37 operates in a manner directly analagous to circuitry 24–26–28 above-discussed for counting heart pulses over a timed interval, periodically loading a latch to preserve the pulse rate reported to the multiplexer 84. The circuitry 37 may be connected to either cuff 50 or 35 — but the cuff 35 is preferred since pulse flow is continuous and not interrupted by a full occluding pressure.

Further, an arrhythmia detector 30 may be employed to signal irregularities in the heart rate or rhythm — all as well known in the art per se. See, for example, Berkovits U.S. Pat. No. 3,345,990 issued Oct. 10, 1967, Haber U.S. Pat. No. 3,144,019 issued Aug. 11, 1964 or Tischler et al U.S. Pat. No. 3,135,264 issued June 2, 1964, the disclosures of which are incorporated herein by reference.

For purposes of determining a subject's temperature, rectal and oral temperature transducers 64 and 65 are included in the composite FIG. 1 equipment. The transducers may comprise, for example, variable resistance elements connected in a bridge configuration — similar to the bridge 12, and may utilize temperature sensitive resistors such as thermistors or the like. The output of the rectal and oral temperature transducers are developed in a difference amplifier 67 or 69 respectively, and one or the other selected by an operator controlled transfer switch 72. This selected temperature value at the transfer pole of the switch 72 is amplified in an amplifier 74; converted to digital form by an analog-to-digital converter 95; and supplied as a further input to the multiplexer 84.

Thus, the composite FIG. 1 apparatus has been shown by the above to measure a subject's vital signs; to supply digital valuations thereof to a multiplexer 84, together with keyboard generated alpha-numeric information and date and time information; and to automatically provide an output record of all that which is supplied as inputs to the multiplexer 84 on any desired time schedule, on an automated basis, such that a written record of a patient's vital signs is automatically generated.

In accordance with one further aspect of the instant invention, a memory 63 may contain permissible bounds for each monitored parameter. When data characterized by any subject parameter is gated out of the multiplexer 84 to the printer 86, the data is also supplied to a digital comparator 65, together with the bounds for the parameter which is read from the store 63 via the multiplexer 84 addressing output of the counter 78. If the comparator 65 notes that the instantaneous value falls outside a permissible range as signalled by the store 63, an alarm element 67 is activated by the comparator 65 to signal a medical attendant that emergency attention is or may be required.

Figure 2:
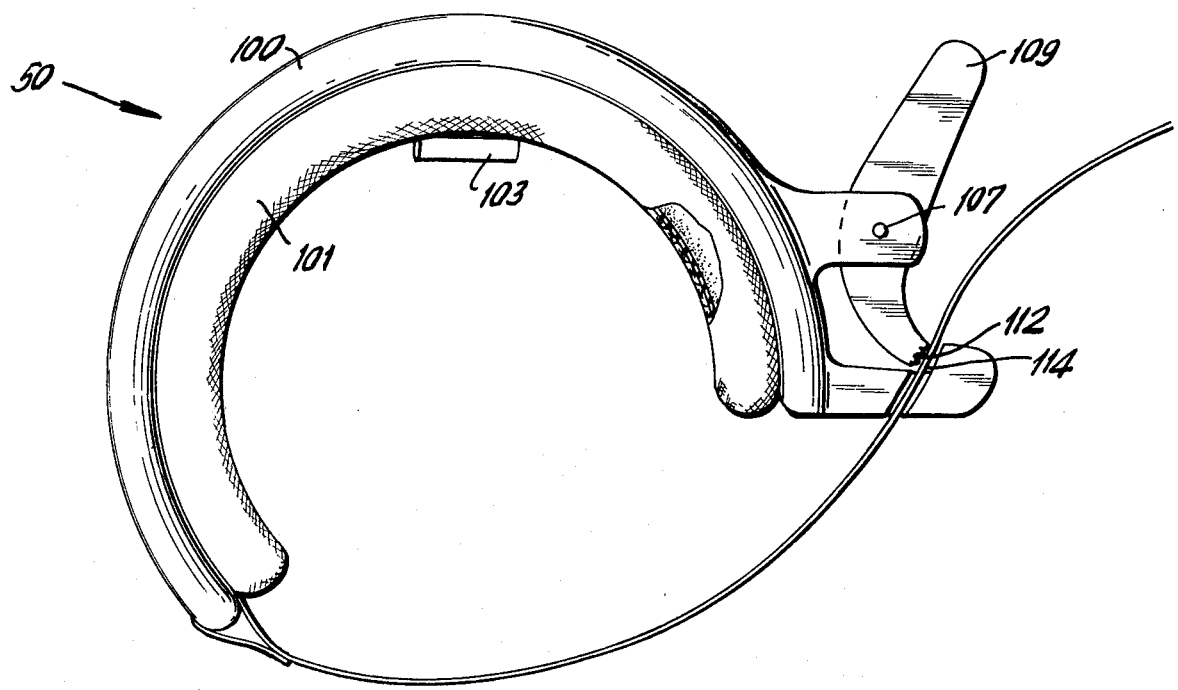
FIG. 2 is a cross-sectional schematical view of a transducer cuff 50 utilized in the FIG. 1 arrangement for occluding a subject's brachial artery, and for reporting the instantaneous cuff occluding pressure and the incidence of Korotkoff sounds.

Referring now to FIG. 2, there is shown a particular embodiment for the brachial artery occluding cuff 50 shown in the FIG. 1 arrangement. The cuff of FIG. 2 includes an outer semirigid frame member 100 having secured therewithin an inflatable bladder which is inflated by the pump 52 of FIG. 1. A lever arm 109 is pivotally affixed to the frame member 100 about a pivot 107, the lever arm being biased in a counter-clockwise direction in the plane of the drawing by structure not shown, e.g., a torsional spring disposed about the pivot pin. A strap 105 is fixed to one end of the outer frame 100, passes through a slot in the frame 100, and is secured in place by serrations in the biased lever arm 109. Finally, the electrical output producing transducer 103 is centrally disposed beneath the bladder.

To operate the cuff 50, the upper portion of the lever 109 is pulled to the left in the drawing, thereby removing the lever serrations from the strap 105 which may then be loosened as required. The subject's arm is then inserted between the inflatable bladder 101 and the strap 105; and the entire engagement tightened about the subject's arm by merely pulling on the remote end of the strap 105. The serrations grip the strap 105, preventing its unintentional loosening.

Turning now to FIG. 3, there is shown an embodiment of the detecting finger cuff 35 which includes a housing 120 having secured thereto a quick release type structure 122, e.g., a Velcro(TM) pad. The cuff 35 includes a central aperture 124 (which includes the transducer element not shown) and a further locking strap 126, e.g., also of the Velcro adhering material, is affixed to the housing 120 to mate with the pad 122 and retain the composite cuff 35 in place. Finally, conductors 128 emanate from the transducer for electrical communication with the composite FIG. 1 apparatus as shown.

Finally, FIG. 4 shows an alternative embodiment for the cuff 35 which includes two members 130 and 132 pivotally secured by a pivot pin 134 and biased together, as via a torsional spring 137 disposed about the pivot. The requisite electrical transducer (e.g., of a piezoelectric material as above discussed) is secured to one of the elements, e.g., the member 132. The cuff 35 of FIG. 4 is simply clipped onto the subject's finger or the like in a manner similar to a common clothespin. Finally, it is observed that a lead 136 again supplies a connection to the active transducer element 138.

The above described arrangements are merely illustrative of the principles of the present invention. Numerous modifications and adaptations thereof will be readily apparent to those skilled in the art without departing from the spirit and scope of the present invention. For example, while several analog-to-digital converters are supplied, it will be obvious to one skilled in the art that only one converter need in fact be employed. Such converter would simply be preceded by an analog multiplexer which is cycled by addressing (control) signals provided by the counter 78.

What is claimed is:

1. In combination in automated medical vital signs monitoring equipment, plural transducer means each providing an electrical signal representative of an associated monitored physical parameter, multiplexing means, signal processing means connecting each of said transducer means with inputs of said multiplexing means, output means connected to the output of said multiplexing means for providing a visable indication of said monitored, physical paramaters, and timing means connected to said multiplexing means for sequentially connecting said signal processing means to said output means, wherein one of said transducer means comprising blood pressure monitoring means for occluding an artery with a monotonically decreasing pressure and means for providing a signal indicative of the occluding pressure, and wherein another of said transducer means includes respiration sensing means for providing a signal indicative of respiration state, said signal processing means associated with said blood pressure monitoring means including correcting means responsive to the output of said respiration monitoring transducer means for correcting the pressure signalled by said blood pressure monitoring transducer means.

2. A combination as in claim 1 wherein said plural transducer means further comprises temperature sensing transducer means.

3. A combination as in claim 2 wherein said temperature sensing transducer means comprises oral transducer means and rectal transducer means formed of a bridge network having one variable resistance element, difference amplifier means connected to each of said oral and rectal bridge circuits, and switch means for selecting the output of the difference amplifier associated with one of said oral and rectal temperature indicating bridge networks.

4. A combination as in claim 1 further comprising means connected to said respiration sensing means for accumulating, over an interval in time, the inspiration dwell period, means for accumulating over a period of time the expiration dwell interval, and divider means connected to said inspiration and expiration accumulating means for providing an output signal representing the ratio of the inspiration dwell interval and expiration dwell interval.

5. A combination as in claim 4 further comprising means connecting said divider means and said multiplexing means.

6. A combination as in claim 1 wherein said timing means base means includes an oscillator, a counter having an input connected to said oscillator, the output of said counter being connected as a control signal to said multiplexer.

7. A combination as in claim 6 further comprising an additional counter for receiving the output of said respiration sensing means, a latch having inputs connected to the output of said counter and outputs connected to said multiplexing means, decoder-sequencing means connected to said latch for sequentially enabling said latch to a sampling mode, and delay means for clearing said additional counter a short time after said latch is operative in a sampling mode.

8. A combination as in claim 7 further comprising means connecting the output of said latch to the input of said multiplexing means.

9. A combination as in claim 1 wherein at least one input to said multiplexing means is of digital form, further comprising memory means for storing parameter bounds, and a digital comparator connected to said memory and to the output of said multiplexing means for providing an alarm condition signalling output when the output of said multiplexing means exceeds permissible bounds therefor.

10. A combination as in claim 9 further comprising alarm signalling means connected to said digital comparator for providing an operator-signalling output indicia when activated by said digital comparator.

11. A combination as in claim 1 wherein said blood pressure monitoring means comprises a detecting cuff a sample and hold circuit, means included in said blood pressure monitoring means for selectively enabling said sample and hold circuit to its sampling mode by a signal supplied thereto by said detecting cuff and to a signal and time coincidence therewith, indicative of first encountered Korotkoff sounds, for loading said sample and hold circuit with the pressure value supplied by said occluding pressure value supplying means.

12. A combination as in claim 11 wherein said occluding means comprises cuff means having an outer frame, an inflatable bladder affixed at the inner surface of said frame means, a lever arm pivotally secured to said frame means and a strap including a slot affixed at one end to said frame means and disposed to pass through said slot in said frame means and be selectively secured in place by said pivoted lever means.

13. A combination as in claim 11 wherein said blood pressure monitoring means further comprises pulse rate monitoring means including counter means for counting pulses produced by said blood pressure monitoring means, a latch having inputs connected to said counter means and outputs connected to said multiplexing means, and timing means for passing the contents of said counter means to said latch and, thereafter, clearing said latch.

14. A combination as in claim 13 further comprising arrhythmia detecting means connected to said pulse monitoring means.

* * * * *

UNITED STATES PATENT OFFICE
CERTIFICATE OF CORRECTION

Patent No. 3,996,928         Dated December 14, 1976

Inventor(s) Alvin J. Marx

It is certified that error appears in the above-identified patent and that said Letters Patent are hereby corrected as shown below:

Claim 3, line 3:  before "formed" insert --each--;

Signed and Sealed this

Eighth Day of March 1977

[SEAL]

*Attest:*

RUTH C. MASON
*Attesting Officer*

C. MARSHALL DANN
*Commissioner of Patents and Trademarks*